(12) United States Patent
Henary et al.

(10) Patent No.: US 10,377,901 B2
(45) Date of Patent: Aug. 13, 2019

(54) NEAR INFRARED ABSORBING FLUORESCENT COMPOSITIONS

(71) Applicant: GEORGIA STATE UNIVERSITY RESEARCH FOUNDATION, INC., Atlanta, GA (US)

(72) Inventors: Maged Henary, Lawrenceville, GA (US); Gabor Patonay, Conyers, GA (US)

(73) Assignee: GEORGIA STATE UNIVERSITY RESEARCH FOUNDATION, INC., Atlanta, GA (US)

( * ) Notice: Subject to any disclaimer, the term of this patent is extended or adjusted under 35 U.S.C. 154(b) by 132 days.

(21) Appl. No.: 15/503,530

(22) PCT Filed: Aug. 12, 2015

(86) PCT No.: PCT/US2015/044889
§ 371 (c)(1),
(2) Date: Feb. 13, 2017

(87) PCT Pub. No.: WO2016/025620
PCT Pub. Date: Feb. 18, 2016

(65) Prior Publication Data
US 2017/0233577 A1    Aug. 17, 2017

Related U.S. Application Data

(60) Provisional application No. 62/036,575, filed on Aug. 12, 2014.

(51) Int. Cl.
*C09B 57/00* (2006.01)
*C09B 23/01* (2006.01)
(Continued)

(52) U.S. Cl.
CPC ........ *C09B 57/007* (2013.01); *C09B 23/0066* (2013.01); *C09B 23/06* (2013.01);
(Continued)

(58) Field of Classification Search
CPC ... C09B 57/007; C09B 23/164; C09B 69/109; C09B 69/105; C09K 11/06;
(Continued)

(56) References Cited

U.S. PATENT DOCUMENTS 5,336,714 A    8/1994  Parham et al.
5,990,197 A   11/1999  Escano et al.
(Continued)

FOREIGN PATENT DOCUMENTS

WO    2013109859 A1    7/2013

OTHER PUBLICATIONS

International Search Report and Written Opinion issued in PCT/US15/44889, dated Nov. 23, 2015.

*Primary Examiner* — Ruiyun Zhang
(74) *Attorney, Agent, or Firm* — Meunier Carlin & Curfman LLC (57) ABSTRACT

Provided herein are heterocyclic near infrared compounds, including near IR compounds defined by Formulae I-V described herein. The near infrared compounds can include a cyanine group, a phthalocyanine group, a naphthalocyanine group, a squaraine group, a carbocyanine group, or a combination thereof. In some embodiments, the near infrared compound can be charged. In some embodiments, the near infrared compound can comprise a cationic group. Compositions comprising the near infrared compounds are also disclosed. In some embodiments, the composition can contain the near infrared compound, a polymer, and an acceptable carrier. In some embodiments, the polymer can include an anionic group. The compositions can be used as
(Continued)

a coating for marking a surface, such as an ink. The compositions can also be used on articles for detecting, identifying, or authenticating the article. Methods of making the compositions described herein are also disclosed.

11 Claims, 2 Drawing Sheets

(51) Int. Cl.
| | |
|---|---|
| *C09B 23/06* | (2006.01) |
| *C09B 23/08* | (2006.01) |
| *C09D 11/104* | (2014.01) |
| *C09D 11/50* | (2014.01) |
| *C09D 11/328* | (2014.01) |
| *C09D 7/41* | (2018.01) |
| *C09B 23/16* | (2006.01) |
| *C09B 69/10* | (2006.01) |
| *C09D 11/03* | (2014.01) |
| *C09D 101/10* | (2006.01) |
| *C09D 167/00* | (2006.01) |
| *C09K 11/02* | (2006.01) |
| *C09K 11/06* | (2006.01) |
| *G01N 21/64* | (2006.01) |

(52) U.S. Cl.
CPC .......... *C09B 23/083* (2013.01); *C09B 23/164* (2013.01); *C09B 69/105* (2013.01); *C09B 69/109* (2013.01); *C09D 7/41* (2018.01); *C09D 11/03* (2013.01); *C09D 11/104* (2013.01); *C09D 11/328* (2013.01); *C09D 11/50* (2013.01); *C09D 101/10* (2013.01); *C09D 167/00* (2013.01); *C09K 11/025* (2013.01); *C09K 11/06* (2013.01); *G01N 21/643* (2013.01); *C09K 2211/1007* (2013.01); *C09K 2211/1044* (2013.01); *G01N 2021/6439* (2013.01)

(58) Field of Classification Search
CPC .......... C09K 11/025; C09K 2211/1044; C09K 2211/1007; C09D 101/10; C09D 167/00; C09D 11/10
USPC ........ 428/690; 313/503; 252/301.35, 301.31, 252/301.32, 301.26, 587; 548/455; 257/432
See application file for complete search history.

(56) References Cited

U.S. PATENT DOCUMENTS

| | | |
|---|---|---|
| 7,820,254 B2 | 10/2010 | Harada et al. |
| 2012/0197026 A1 | 8/2012 | Maeda et al. |
| 2013/0147345 A1* | 6/2013 | Maeda ................ C09B 23/0066 313/503 |

* cited by examiner

NEAR INFRARED ABSORBING FLUORESCENT COMPOSITIONS

CROSS-REFERENCE TO RELATED APPLICATIONS

This application is a national stage application under 35 U.S.C. 371 based on application PCT/US2015/044889 filed Aug. 12, 2015, which claims the benefit of U.S. Provisional Application No. 62/036,575 filed Aug. 12, 2014, the disclosures of which are hereby incorporated in their entirety and for all purposes.

FIELD

This disclosure relates generally to near infrared absorbing fluorescent compounds and compositions comprising the compounds.

BACKGROUND

Colorants are widely used in many applications to provide useful and aesthetic appearance to articles and printed images. Many commonly known colorants include a dye which is covalently attached via copolymerization to a polymer. Copolymerization is generally conducted at high temperatures, therefore requiring the copolymerized dyes to have high thermal stability. There is a need for improved methods to produce colorants containing dyes. The compounds, compositions, and methods disclosed herein address these and other needs.

SUMMARY

Provided herein are heterocyclic near-IR compounds, including near IR compounds defined by Formulae I-V described herein. The near infrared compounds can include a cyanine group, a phthalocyanine group, a naphthalocyanine group, a squaraine group, a carbocyanine group, or a combination thereof. The near infrared compounds can be symmetrical or non-symmetrical. In some embodiments, the near infrared compound can be charged. In some embodiments, the near infrared compound can comprise a cationic group. For example, the compound can comprise a plurality of cations such as from 2 to 4 cations.

Compositions comprising the near infrared compounds described herein are also disclosed. In some embodiments, the composition contains a near infrared compound and an acceptable carrier. The acceptable carrier can include a solvent. The solvent can include water, an alcohol, a ketone, an ester, or mixtures thereof. The near infrared compound can be dispersed or dissolved in the carrier. The near infrared compound can be in an amount of from about 0.001% to about 5% by weight of the composition.

In some embodiments, the composition can contain a near infrared compound, a polymer, and an acceptable carrier. In some embodiments, the polymer can include a functional group reactive with the near infrared compound. The near infrared compound can be covalently or non-covalently linked to the polymer. For example, the near infrared compound can interact with the polymer through electrostatic forces, dipole-dipole interactions, hydrogen bonding, hydrophobic interactions, van der Waals forces, or combinations thereof.

The polymer in the composition can be selected from substituted and unsubstituted polyamides, polyimides, polyesters, polyacrylates, polyacrylic acids, polyethers, vinylic polymers, polyimines, polysiloxanes, polyurethanes, polythioethers, polycarbonates, polyolefins, polyarylalkylenes, polysilanes, polyesteramides, polyacetal, polysulfones, polystyrenes, polyacrylamides, polyvinyl alcohols, polyphosphonite, polyphosphonate, cellulose, derivatives thereof, copolymers thereof, and blends thereof. In some embodiments, the polymer can include an anionic group. For example, the polymer can include an anionic group such as sulfonate, sulfate, borate, carboxylate, phosphonate, phosphate, thioacetate, thiols, thiosulphate, oxalate, nitro group, alkoxide, salts thereof, and combinations thereof.

Method of making the compositions described herein are also disclosed. The method can include dissolving the polymer in a first solvent to form a polymer solution, dissolving the near infrared compound in a second solvent to form a near infrared solution, combining the near infrared solution and the polymer solution, and optionally evaporating the first solvent, the second solvent, or a combination thereof. The method can further include adding a third solvent to the polymer solution when combining the near infrared solution and the polymer solution. Dissolving the polymer in the first solvent can include heating the first solvent and optionally, cooling the polymer solution formed. The first solvent can include water and the second solvent can include a volatile organic solvent.

The methods described herein can provide for the dispersion of the near infrared compound in a water-dispersible polymer without requiring the near infrared compound to be present during a polymerization process. These methods can be used to prepare compositions without subjecting the near infrared compound to a high temperature copolymerization and dispersion processes.

The compositions can be used as a coating for marking a surface by printing, spraying, painting, or other methods for the purpose of identification and authentication of objects. The compositions can be used as an ink. The compositions can also be used on articles. For example, the compositions can be used for detecting, identifying, or authenticating the article.

BRIEF DESCRIPTION OF THE DRAWINGS

The accompanying drawings, which are incorporated in and constitute a part of this specification, illustrate several embodiments of the disclosure and together with the description, serve to explain the principles of the disclosure.

FIG. 1 is a flow-diagram showing an apparatus that can be used in a method for identifying near infrared dyes molecularly dispersed in a polymeric composition in a near infrared apparatus. The apparatus includes a light source (1) capable of emitting radiation in the visible and NIR region which illuminates the polymeric ink sample (2) through a first wavelength selector (3) e.g. monochromator or interference filter. A second wavelength selector (4) and a NIR sensitive photodetector (5) is placed at 90 degree or less angle. The light source (1), the wavelength selectors (3 and 4) and photodetector (5) are all arranged on two sides of a triangle to minimize scattering light entering the detector. In addition to the wavelength selector a polarizer may be inserted in the light path to further decrease scattering as surface reflected light is usually polarized. The light source (1) may be replaced with lasers, preferable semiconductor lasers. The output of the photodetector (5) is provided to level adjustment amplifier (6) or a neutral filter to adjust light levels if necessary, the output of which is provided to an integrated circuit digital multimeter (7). The output of the digital multimeter is connected to a computer display so as to provide a numeral and graphical indication of the amount of the luminous flux at the predetermined wavelength (preferably at or near the emission maxima) emitted by the near infrared dye molecularly dispersed in the polymer. Detection at longer wavelengths than the dye fluorescence maximum may be necessary to reduce the effect of scattering in case of highly reflective or shiny surfaces.

FIG. 2 shows a drawing of an apparatus that can be used for detecting near infrared dyes. The apparatus include a laser diode light source (1) capable of emitting radiation in the NIR region that is collimated through a collimating lens (2), and illuminates the NIRF-marked or printed article (4) through an optical filter (3). A focusing lens (5) and a beam compressor are placed at 30 degrees or less angle. The laser diode light source and the collimating lens are arranged to minimize scattered light from entering the detector. An optical filter (6) is placed between the compressor lenses (7 and 8) to select the wavelength of fluorescence from the NIRF-marked or printed article which is focused on the photodetector. A current to voltage converter is connected to photodetector to amplify the detector signal. The arrangement and the electronic circuitry of the current to voltage amplifier (10) is widely known and the routines of amplifying and processing the photodetector signal are also well known. The signal from the current to voltage converter circuit is detected by a threshold detector (11). The threshold level of the threshold detector is set at the level required to minimize any interference from unmarked or printed articles. The presence of marked articles in front of the preferred apparatus is indicated by the light-emitting diode (LED) indicator (12).

DESCRIPTION

Figure 1:
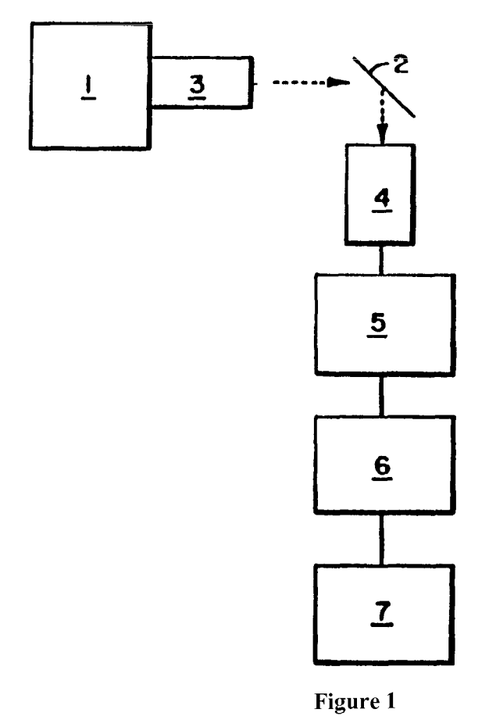
Figure 2:
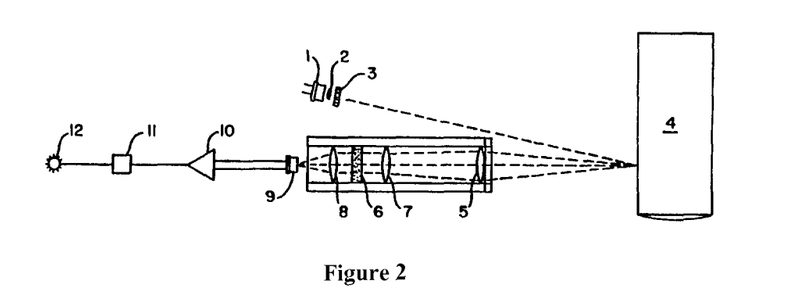
Figure 3:
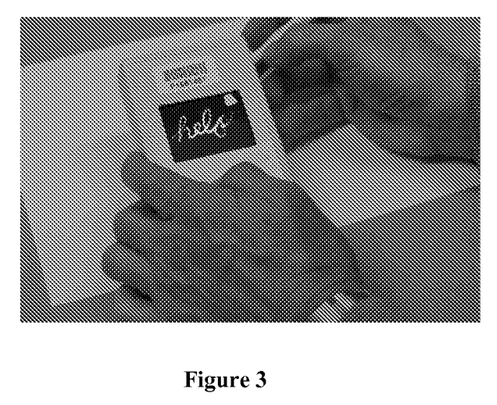
FIG. 3 shows an image on a near infrared fluorescence viewing device. The image is from an invisible writing on an article positioned in front of the device. The writing "help" is revealed as bright white fluorescence against a dark background.
Figure 4:
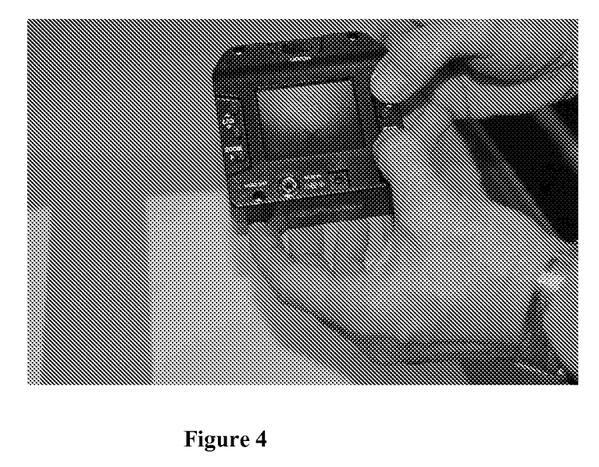
FIG. 4 shows a near infrared emission image on a NiteMax Ultra digital night vision viewer camera. The image is from an invisible writing on an article positioned in front of the device. The marks "X and O" are revealed as dark marks against a light background.

The present disclosure may be understood more readily by reference to the following detailed description of preferred embodiments of the invention and the Examples included therein and to the Figures and their previous and following description.

Before the present compounds, compositions, and/or methods are disclosed and described, it is to be understood that the terminology used herein is for the purpose of describing particular embodiments only and is not intended to be limiting.

As used in the specification and the appended claims, the singular forms "a," "an" and "the" include plural referents unless the context clearly dictates otherwise. Thus, for example, reference to "a compound of Formula I" includes mixtures of compounds of Formula I, reference to "an acceptable carrier" includes mixtures of two or more such carriers, and the like.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

In this specification and in the claims which follow, reference will be made to a number of terms which shall be defined to have the following meanings:

The term "alkyl" includes both "unsubstituted alkyls" and "substituted alkyls", the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, a phosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "alkyl" as used herein means an alkyl group, as defined above, but having from one to twenty carbons, more preferably from one to ten carbon atoms in its backbone structure. Likewise, "alkenyl" and "alkynyl" have similar chain lengths.

The alkyl groups can also contain one or more heteroatoms within the carbon backbone. Examples include oxygen, nitrogen, sulfur, and combinations thereof. In certain embodiments, the alkyl group contains between one and four heteroatoms.

The term "heteroalkyl", as used herein, refers to straight or branched chain, or cyclic carbon-containing radicals, or combinations thereof, containing at least one heteroatom. Suitable heteroatoms include, but are not limited to, O, N, Si, P, Se, B, and S, wherein the phosphorous and sulfur atoms are optionally oxidized, and the nitrogen heteroatom is optionally quaternized. Heteroalkyls can be substituted as defined above for alkyl groups.

The term "alkylthio" refers to an alkyl group, as defined above, having a sulfur radical attached thereto. In preferred embodiments, the "alkylthio" moiety is represented by one of —S-alkyl, —S-alkenyl, and —S-alkynyl. Representative alkylthio groups include methylthio, ethylthio, and the like. The term "alkylthio" also encompasses cycloalkyl groups, alkene and cycloalkene groups, and alkyne groups. "Arylthio" refers to aryl or heteroaryl groups. Alkylthio groups can be substituted as defined above for alkyl groups.

"Alkenyl" and "Alkynyl", as used herein, refer to unsaturated aliphatic groups containing one or more double or triple bonds analogous in length (e.g., $C_2$-$C_{30}$) and possible substitution to the alkyl groups described above.

"Aryl", as used herein, refers to 5-, 6- and 7-membered aromatic rings. The ring can be a carbocyclic, heterocyclic, fused carbocyclic, fused heterocyclic, bicarbocyclic, or biheterocyclic ring system, optionally substituted as described above for alkyl. Broadly defined, "Ar", as used herein, includes 5-, 6- and 7-membered single-ring aromatic groups that can include from zero to four heteroatoms. Examples include, but are not limited to, benzene, pyrrole, furan, thiophene, imidazole, oxazole, thiazole, triazole, pyrazole, pyridine, pyrazine, pyridazine and pyrimidine. Those aryl groups having heteroatoms in the ring structure can also be referred to as "heteroaryl", "aryl heterocycles", or "heteroaromatics". The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, and —CN. The term "Ar" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocycles, or both rings are aromatic.

"Alkylaryl" or "aryl-alkyl", as used herein, refers to an alkyl group substituted with an aryl group (e.g., an aromatic or hetero aromatic group).

"Heterocycle" or "heterocyclic", as used herein, refers to a cyclic radical attached via a ring carbon or nitrogen of a monocyclic or bicyclic ring containing 3-10 ring atoms, and preferably from 5-6 ring atoms, containing carbon and one to four heteroatoms each selected from non-peroxide oxygen, sulfur, and N(Y) wherein Y is absent or is H, O, (C$_{1-4}$) alkyl, phenyl or benzyl, and optionally containing one or more double or triple bonds, and optionally substituted with one or more substituents. The term "heterocycle" also encompasses substituted and unsubstituted heteroaryl rings. Examples of heterocyclic ring include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl.

"Heteroaryl", as used herein, refers to a monocyclic aromatic ring containing five or six ring atoms containing carbon and 1, 2, 3, or 4 heteroatoms each selected from non-peroxide oxygen, sulfur, and N(Y) where Y is absent or is H, O, (C$_1$-C$_8$) alkyl, phenyl or benzyl. Non-limiting examples of heteroaryl groups include furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide), quinolyl (or its N-oxide) and the like. The term "heteroaryl" can include radicals of an ortho-fused bicyclic heterocycle of about eight to ten ring atoms derived therefrom, particularly a benz-derivative or one derived by fusing a propylene, trimethylene, or tetramethylene diradical thereto. Examples of heteroaryl include, but are not limited to, furyl, imidazolyl, triazolyl, triazinyl, oxazoyl, isoxazoyl, thiazolyl, isothiazoyl, pyraxolyl, pyrrolyl, pyrazinyl, tetrazolyl, pyridyl (or its N-oxide), thientyl, pyrimidinyl (or its N-oxide), indolyl, isoquinolyl (or its N-oxide), quinolyl (or its N-oxide), and the like.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O— alkenyl, and —O-alkynyl. Aroxy can be represented by —O-aryl or O-heteroaryl, wherein aryl and heteroaryl are as defined below. The alkoxy and aroxy groups can be substituted as described above for alkyl.

The terms "amine" and "amino" are art-recognized and refer to both unsubstituted and substituted amines, e.g., a moiety that can be represented by the general formula: —NR$_9$R$_{10}$ or NR$_9$R$_{10}$R'$_{10}$, wherein R$_9$, R$_{10}$, and R'$_{10}$ each independently represent a hydrogen, an alkyl, an alkenyl, —(CH$_2$)$_m$—R'$_8$ or R$_9$ and R$_{10}$ taken together with the N atom to which they are attached complete a heterocycle having from 4 to 8 atoms in the ring structure; R'$_8$ represents an aryl, a cycloalkyl, a cycloalkenyl, a heterocycle or a polycycle; and m is zero or an integer in the range of 1 to 8. In some embodiments, only one of R$_9$ or R$_{10}$ can be a carbonyl, e.g., R$_9$, R$_{10}$ and the nitrogen together do not form an imide. In some embodiments, the term "amine" does not encompass amides, e.g., wherein one of R$_9$ and R$_{10}$ represents a carbonyl. In some embodiments, R$_9$ and R$_{10}$ (and optionally R'$_{10}$) each independently represent a hydrogen, an alkyl or cycloakyl, an alkenyl or cycloalkenyl, or alkynyl. Thus, the term "alkylamine" as used herein means an amine group, as defined above, having a substituted (as described above for alkyl) or unsubstituted alkyl attached thereto, i.e., at least one of R$_9$ and R$_{10}$ is an alkyl group.

The term "amido" is art-recognized as an amino-substituted carbonyl and includes a moiety that can be represented by the general formula —CONR$_9$R$_{10}$ wherein R$_9$ and R$_{10}$ are as defined above.

"Halogen", as used herein, refers to fluorine, chlorine, bromine, or iodine.

"Nitro", as used herein, refers to —NO$_2$.

"Sulfhydryl", as used herein, refers to —SH.

"Hydroxyl", as used herein, refers to —OH.

"Sulfonyl" as used herein, refers to —SO$_2$—.

The term "carbonyl" is art-recognized and includes such moieties as can be represented by the general formula —CO—XR$_{11}$, or —X—CO—R'$_{11}$, wherein X is a bond or represents an oxygen or a sulfur, and R$_{11}$ represents a hydrogen, an alkyl, a cycloalkyl, an alkenyl, an cycloalkenyl, or an alkynyl, R'$_{11}$ represents a hydrogen, an alkyl, a cycloalkyl, an alkenyl, an cycloalkenyl, or an alkynyl. Where X is an oxygen and R$_{11}$ or R'$_{11}$ is not hydrogen, the formula represents an "ester". Where X is an oxygen and R is as defined above, the moiety is referred to herein as a carboxyl group, and particularly when R is a hydrogen, the formula represents a "carboxylic acid". Where X is an oxygen and R'$_{11}$ is hydrogen, the formula represents a "formate". In general, where the oxygen atom of the above formula is replaced by sulfur, the formula represents a "thiocarbonyl" group. Where X is a sulfur and R or R'$_{11}$ is not hydrogen, the formula represents a "thioester." Where X is a sulfur and R$_{11}$ is hydrogen, the formula represents a "thiocarboxylic acid." Where X is a sulfur and R'$_{11}$ is hydrogen, the formula represents a "thioformate." On the other hand, where X is a bond, and $R_{11}$ is not hydrogen, the above formula represents a "ketone" group. Where X is a bond, and $R_{11}$ is hydrogen, the above formula represents an "aldehyde" group.

The term "substituted" as used herein, refers to all permissible substituents of the compounds described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, preferably 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aryloxy, substituted aryloxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, aminoacid, peptide, and polypeptide groups.

It is understood that "substitution" or "substituted" includes the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc.

Unless the number of carbons is otherwise specified, "lower" (for example, "lower alkyl", "lower alkoxy" as used herein means a group, as defined herein, but having from one to ten carbons, more preferably from one to six carbon atoms in its backbone structure.

Compounds

Compounds that can emit light having a first wavelength are disclosed herein. In some embodiments, the compounds can be near infrared compounds. In some examples, the near infrared compound can include a cyanine group, a phthalocyanine group, a naphthalocyanine group, a squaraine group, a carbocyanine group, or a combination thereof. The compounds can be symmetrical or non-symmetrical.

In some embodiments, the compounds can be charged. In some examples, the compound can include a cationic or an anionic group. In some embodiments, the compound can include a plurality of cations. For example, the compound can include one, two, three, four, or more cationic groups. In some embodiments, the compound can include a cationic group such as a quaternary ammonium group or an iminium group. In some embodiments, the compound can include an anionic group such as sulfonate, sulfate, borate, carboxylate, phosphonate, phosphate, thioacetate, thiols, thiosulphate, oxalate, nitro group, alkoxide, salts thereof, and combinations thereof. In some examples, the compound can be zwitterionic.

In some examples, the compound can have a structure according to Formula I:

Formula I or a salt or a hydrate thereof, wherein R and R' are independently selected from the group consisting of hydrogen; substituted or unsubstituted alkyl; substituted or unsubstituted cycloalkyl; substituted or unsubstituted alkenyl; substituted or unsubstituted alkynyl; substituted or unsubstituted heterocyclyl; substituted or unsubstituted cycloalkenyl; substituted or unsubstituted heterocycloalkenyl; substituted or unsubstituted aryl; substituted or unsubstituted heteroaryl; substituted or unsubstituted heteroalkyl; substituted or unsubstituted alkylaryl; substituted or unsubstituted alkylheteroaryl; and R" and R'" are independently selected from the group consisting of hydrogen; halogen; alkyl, —$OR^1$; —$NR^1R_2$; —$NO_2$; —$CF_3$; —CN; —$C_2R^1$; —$SR^1$; —$N_3$; $C(=O)R^1$; —$C(=O)OR^1$; —$OC(=O)R^1$; —$O(CR^1R_2)_rC(=O)R_1$; —$C(=O)NR^1R_2$; —$NR^1C(=O)R^2$; —$O(CR^1R_2)_rNR^2C(=O)R^1$; —$O(CR^1R_2)_rNR^2SO_2R^1$; —$OC(=O)NR^1R_2$; —$NR^1C(=O)OR^2$; —$SO_2R^1$; —$SO_2NR^1R_2$; and —$NR^1SO_2R^2$; wherein $R^1$ and $R^2$ are individually hydrogen; substituted or unsubstituted alkyl; substituted or unsubstituted alkenyl; substituted or unsubstituted alkynyl; substituted or unsubstituted cycloalkyl; substituted or unsubstituted heterocyclyl; substituted or unsubstituted cycloalkenyl, substituted or unsubstituted heterocycloalkenyl, substituted or unsubstituted aryl, substituted or unsubstituted heteroaryl, substituted or unsubstituted arylalkyl, substituted or unsubstituted heteroalkyl, or substituted or unsubstituted alkylheteroaryl; and r is an integer from 1 to 6.

In some examples, the compound has a structure represented by Formula Ia, Ib, or Ic:

Formula Ia

-continued

Formula Ib

Formula Ic or a salt or a hydrate thereof, wherein R, R', R", and R'" are as described herein.

R and R' or R" and R'" can be the same or different. In some examples, R and R' or R" and R'" are different.

In some embodiments, R and R' can be independently selected from hydrogen, lower alkyl, lower alkoxy, halogen, aryloxy, lower alkylthio, arylthio, lower alkylsulfonyl; arylsulfonyl; lower alkylsulfonyamino, arylsulfonylamino, cycloalkylsulfonylamino, carboxy, unsubstituted and substituted carbamoyl and sulfamoyl, lower alkoxycarbonyl, hydrogen, lower alkanoyloxy, amino, alkylamino, arylamino, dialkylamino, substituted alkylamino, or substituted arylamino. For example, R and R' can be independently selected from the group consisting of hydrogen, substituted or unsubstituted alkyl-aryl. In certain embodiments, R and R' can be independently selected from the group consisting of benzyl, phenyl-ethyl, phenyl-propyl, and phenyl-butyl.

In some embodiments, R and R' are independently selected from substituted or unsubstituted alkyl and alkylaryl; and R" and R'" are independently selected from hydrogen; halogen; alkyl, —OR$^1$; —NR$^1$R$_2$; —CN; —C(=O)OR$^1$; —OC(=O)R$^1$; C(=O)R$^1$; —SO$_2$R$^1$; —SO$_2$NR$^1$R$_2$; and —NR$^1$SO$_2$R$^2$; wherein R$^1$ and R$^2$ are individually hydrogen; or substituted or unsubstituted alkyl. In some embodiments, R" and R'" can both be hydrogen.

In some embodiments, R" and R'" are not the same. In some embodiments, R' and R' are not the same. For example, R can be phenyl-ethyl and R' is phenyl-propyl or phenyl-butyl. In some embodiments, when R is a substituted or unsubstituted methyl, R' is not a substituted or unsubstituted methyl; when R is a substituted or unsubstituted ethyl, R' is not a substituted or unsubstituted ethyl; when R is a substituted or unsubstituted propyl, R' is not a substituted or unsubstituted propyl; when R is a substituted or unsubstituted butyl, R' is not a substituted or unsubstituted butyl; and so forth. In some embodiments, when R" is hydrogen, R'" is not hydrogen; when R" is a carboxylate, R'" is not a carboxylate; when R" is a sulfate or sulfonate, R'" is not a sulfate or sulfonate; when R" is a phosphate or phosphonate, R'" is not a phosphate or phosphonate; when R" is an alkoxy group, R'" is not an alkoxy group.

In some embodiments, R, R', R", and R'" can be independently charged. In some examples, R, R', R", and R'" can independently include a cationic or an anionic group. In some embodiments, R, R', R", and R'" can include a cationic group such as a quaternary ammonium group or an iminium group. In some embodiments, R, R', R", and R'" can include an anionic group such as sulfonate, sulfate, borate, carboxylate, phosphonate, phosphate, thioacetate, thiols, thiosulphate, oxalate, nitro group, alkoxide, salts thereof, and combinations thereof. In some examples, the compound represented by Formula I, Ia, Ib, and Ic can include a plurality of cations. In some examples, the compound can include one, two, three, four, or more cationic groups.

In some examples, the compound can have a structure according to Formula II:

Formula II or a salt or a hydrate thereof, wherein R and R' are independently selected from the group consisting of hydrogen; substituted or unsubstituted alkyl; substituted or unsubstituted cycloalkyl; substituted or unsubstituted alkenyl; substituted or unsubstituted alkynyl; substituted or unsubstituted heterocyclyl; substituted or unsubstituted cycloalkenyl; substituted or unsubstituted heterocycloalkenyl; substituted or unsubstituted aryl; substituted or unsubstituted heteroaryl; substituted or unsubstituted heteroalkyl; substituted or unsubstituted alkylaryl; substituted or unsubstituted alkylheteroaryl;

R" and R'" can be independently selected from the group consisting of hydrogen; alkyl, —OR$^1$; —NR$^1$R$_2$; —NR$^1$R$^2$R$_3$; —NO$_2$; —CF$_3$; —CN; —C$_2$R'; —SR'; —N$_3$; C(=O) R$^1$; —C(=O)O R$^1$; —OC(=O) R$^1$; —O(CR$^1$R$_2$)$_r$C(=O) R$^1$; —C(=O)NR$^1$R$_2$; —NR$^1$C(=O) R$^2$; —O(CR$^1$R$_2$)$_r$NR$^2$C(=O)R$_1$; —O(CR$^1$R$_2$)$_r$NR$^2$SO$_2$R$^1$; —OC(=O)NR$^1$R$_2$; —NR$^1$C(=O)OR$^2$; —SO$_2$R$^1$; —SO$_2$NR$^1$R$_2$; and —NR$^1$SO$_2$R$^2$; wherein R$^1$, R$^2$, and R$^3$ are individually hydrogen; substituted or unsubstituted alkyl; alkenyl; alkynyl; cycloalkyl; heterocyclyl; cycloalkenyl, heterocycloalkenyl, aryl, heteroaryl, arylalkyl, heteroalkyls, aryl, alkylaryl, alkylheteroaryl; and r is an integer from 1 to 6, and n can be an integer from 1 to 6.

In some examples, the compound has a structure represented by Formula IIa, IIb, or IIc:

Formula IIa

-continued

Formula IIb

Formula IIc or a salt or a hydrate thereof, wherein R, R', R", and R'" are as described herein.

R and R' can be the same or different. In some embodiments, R and R' can all be hydrogen.

In some embodiments, R and R' can be independently selected from hydrogen, lower alkyl, lower alkoxy, halogen, aryloxy, lower alkylthio, arylthio, lower alkylsulfonyl; arylsulfonyl; lower alkylsulfonyamino, arylsulfonylamino, cycloalkylsulfonylamino, carboxy, unsubstituted and substituted carbamoyl and sulfamoyl, lower alkoxycarbonyl, hydrogen, lower alkanoyloxy, amino, alkylamino, arylamino, dialkylamino, substituted alkylamino, or substituted arylamino. For example, R and R' can be independently selected from the group consisting of hydrogen, substituted or unsubstituted alkyl, substituted or unsubstituted aryl, and substituted or unsubstituted alkyl-aryl. In certain embodiments, R and R' can be independently selected from the group consisting of methyl, ethyl, propyl, butyl, phenylethyl, phenyl-propyl, phenyl-butyl, and phenyl-sulfite.

In some embodiments, R and R' are independently selected from substituted or unsubstituted alkyl and alkylaryl and R" and R'" are independently selected from hydrogen; halogen; alkyl, —OR$^1$; —NR$^1$R$_2$; —CN; —C(=O) OR$^1$; —OC(=O)R$^1$; C(=O)R$^1$; —SO$_2$R$^1$; —SO$_2$NR$^1$R$_2$; and —NR$^1$SO$_2$R$^2$; wherein R$^1$ and R$^2$ are individually hydrogen; or substituted or unsubstituted alkyl. In some embodiments, R" and R'" can all be hydrogen.

In some embodiments, R" and R'" are not the same. In some embodiments, R' and R' are not the same. For example, R can be ethyl and R' is propyl or butyl. In some embodiments, when R is a substituted or unsubstituted methyl, R' is not a substituted or unsubstituted methyl; when R is a substituted or unsubstituted ethyl, R' is not a substituted or unsubstituted ethyl; when R is a substituted or unsubstituted propyl, R' is not a substituted or unsubstituted propyl; when R is a substituted or unsubstituted butyl, R' is not a substituted or unsubstituted butyl; and so forth. In some embodiments, when R" is hydrogen, R'" is not hydrogen; when R" is a carboxylate, R'" is not a carboxylate; when R" is a sulfate or sulfonate, R'" is not a sulfate or sulfonate; when R" is a phosphate or phosphonate, R'" is not a phosphate or phosphonate; when R" is an alkoxy group, R'" is not an alkoxy group.

In some embodiments, R, R', R", and R'" can be independently charged. In some examples, R, R', R", and R'" can independently include a cationic or an anionic group. In some embodiments, R, R', R", and R'" can independently include a cationic group such as a quaternary ammonium group or an iminium group. In some embodiments, R, R', R", and R'" can independently include an anionic group such as sulfonate, sulfate, borate, carboxylate, phosphonate, phosphate, thioacetate, thiols, thiosulphate, oxalate, nitro group, alkoxide, salts thereof, and combinations thereof. In some examples, the compound represented by Formula II, IIa, IIb, or IIc can include a plurality of cations. In some examples, the compound can include one, two, three, four, or more cationic groups.

In some embodiments, n can be 1, 2, 3, 4, 5, or 6.

In some examples, the compound can have a structure according to Formula III:

Formula III or a salt or a hydrate thereof, wherein R and R' are independently selected from the group consisting of hydrogen; substituted or unsubstituted alkyl; substituted or unsubstituted cycloalkyl; substituted or unsubstituted alkenyl; substituted or unsubstituted alkynyl; substituted or unsubstituted heterocyclyl; substituted or unsubstituted cycloalkenyl; substituted or unsubstituted heterocycloalkenyl; substituted or unsubstituted aryl; substituted or unsubstituted heteroaryl; substituted or unsubstituted heteroalkyl; substituted or unsubstituted alkylaryl; substituted or unsubstituted alkylheteroaryl; and A is selected from the group consisting of hydrogen; alkyl, —OR$^1$; —NR$^1$R$_2$; —NR$^1$R$_2$R$^3$; —NO$_2$; —CF$_3$; —CN; —C$_2$R'; —SR'; —N$_3$; C(=O) R$^1$; —C(=O)O R$^1$; —OC(=O) R$^1$; —O(CR$^1$R$_2$)$_r$C(=O) R$^1$; —C(=O)NR$^1$R$_2$; —NR$^1$C(=O)R$^2$; —O(CR$^1$R$_2$)$_r$NR$^2$C(=O)R$_1$; —O(CR$^1$R$_2$)$_r$NR$^2$SO$_2$R$^1$; —OC(=O)NR$^1$R$_2$; —NR$^1$C (=O)OR$^2$; —SO$_2$R$^f$; —SO$_2$NR$^1$R$_2$; and —NR$^1$SO$_2$R$^2$; wherein R$^1$, R$^2$, and R$^3$ are individually hydrogen; substituted or unsubstituted alkyl; alkenyl; alkynyl; cycloalkyl; heterocyclyl; cycloalkenyl, heterocycloalkenyl, aryl, heteroaryl, arylalkyl, heteroalkyls, aryl, alkylaryl, alkylheteroaryl; and r is an integer from 1 to 6.

In some examples, the compound has a structure represented by Formula IIIa:

Formula IIIa or a salt or a hydrate thereof, wherein R and R' are as described herein, and n and m are independently an integer from 0 to 6.

R and R' can be the same or different. In some embodiments, R and R' can all be hydrogen.

In some embodiments, R and R' can be independently selected from hydrogen, lower alkyl, lower alkoxy, halogen, aryloxy, lower alkylthio, arylthio, lower alkylsulfonyl; arylsulfonyl; lower alkylsulfonyamino, arylsulfonylamino, cycloalkylsulfonylamino, carboxy, unsubstituted and substituted carbamoyl and sulfamoyl, lower alkoxycarbonyl, hydrogen, lower alkanoyloxy, amino, alkylamino, arylamino, dialkylamino, substituted alkylamino, or substituted arylamino. For example, R and R' can be independently selected from the group consisting of hydrogen, substituted or unsubstituted alkyl, substituted or unsubstituted aryl, and substituted or unsubstituted alkyl-aryl. In certain embodiments, R and R' can be independently selected from the group consisting of methyl, ethyl, propyl, butyl, phenyl-ethyl, phenyl-propyl, phenyl-butyl, and phenyl-sulfite.

In some embodiments, R and R' are independently selected from substituted or unsubstituted alkyl and alkylaryl; and A is selected from hydrogen; halogen; alkyl, —OR$^1$; —NR$^1$R$_2$; —CN; —C(=O)OR$^1$; —OC(=O)R$^1$; C(=O)R$^1$; —SO$_2$R$^1$; —SO$_2$NR$^1$R$_2$; and —NR$^1$SO$_2$R$^2$; wherein R$^1$ and R$^2$ are individually hydrogen; or substituted or unsubstituted alkyl. In some embodiments, A can be hydrogen, substituted or unsubstituted alkyl, carboxylate, or sulfonate.

In some embodiments, R' and R' are not the same. For example, R can be ethyl and R' is propyl or butyl. In some embodiments, when R is a substituted or unsubstituted methyl, R' is not a substituted or unsubstituted methyl; when R is a substituted or unsubstituted ethyl, R' is not a substituted or unsubstituted ethyl; when R is a substituted or unsubstituted propyl, R' is not a substituted or unsubstituted propyl; when R is a substituted or unsubstituted butyl, R' is not a substituted or unsubstituted butyl; and so forth. In some embodiments, when R' and R' are the same, A is not hydrogen or a carboxylate group.

In some embodiments, n and m can independently be 0, 1, 2, 3, 4, 5, or 6.

In some embodiments, R and R' can be independently charged. In some examples, R and R' can independently include a cationic or an anionic group. In some embodiments, R and R' can independently include a cationic group such as a quaternary ammonium group or an iminium group. In some embodiments, R and R' can independently include an anionic group such as sulfonate, sulfate, borate, carboxylate, phosphonate, phosphate, thioacetate, thiols, thiosulphate, oxalate, nitro group, alkoxide, salts thereof, and combinations thereof. In some examples, the compound represented by Formula III or IIIa can be include a plurality of cations. In some examples, the compound can include one, two, three, four, or more cationic groups.

In some examples, the compound can have a structure according to Formula IV:

Formula IV or a salt or a hydrate thereof, wherein R and R' are independently selected from the group consisting of hydrogen; substituted or unsubstituted alkyl; substituted or unsubstituted cycloalkyl; substituted or unsubstituted alkenyl; substituted or unsubstituted alkynyl; substituted or unsubstituted heterocyclyl; substituted or unsubstituted cycloalkenyl; substituted or unsubstituted heterocycloalkenyl; substituted or unsubstituted aryl; substituted or unsubstituted heteroaryl; substituted or unsubstituted heteroalkyl; substituted or unsubstituted alkylaryl; substituted or unsubstituted alkylheteroaryl; and R" and R'" can be independently selected from the group consisting of hydrogen; alkyl, —OR$^1$; —NR$^1$R$_2$; —NR$^1$R$^2$R$_3$; —NO$_2$; —CF$_3$; —CN; —C$_2$R'; —SR'; —N$_3$; C(=O) R$^1$; —C(=O)O R$^1$; —OC(=O) R$^1$; —O(CR$^1$R$_2$)$_r$C(=O) R$^1$; —C(=O)NR$^1$R$_2$; —NR$^1$C(=O) R$^2$; —O(CR$^1$R$_2$)$_r$NR$^2$C(=O)R$_1$; —O(CR$^1$R$_2$)$_r$NR$^2$SO$_2$R$^1$; —OC(=O)NR$^1$R$_2$; —NR$^1$C(=O)OR$^2$; —SO$_2$R$^1$; —SO$_2$NR$^1$R$_2$; and —NR$^1$SO$_2$R$^2$; wherein R$^1$, R$^2$, and R$^3$ are individually hydrogen; substituted or unsubstituted alkyl; alkenyl; alkynyl; cycloalkyl; heterocyclyl; cycloalkenyl, heterocycloalkenyl, aryl, heteroaryl, arylalkyl, heteroalkyls, aryl, alkylaryl, alkylheteroaryl; and r is an integer from 1 to 6. The compound of Formula IV can be symmetrical or non-symmetrical.

In some examples, the compound has a structure represented by Formula IVa:

Formula IVa or a salt or a hydrate thereof, wherein A, R, R', R", and R'" are as described herein, and n and m are independently an integer from 0 to 6.

R and R' can be the same or different. In some embodiments, R and R' can all be hydrogen.

In some embodiments, R and R' can be independently selected from hydrogen, lower alkyl, lower alkoxy, halogen, aryloxy, lower alkylthio, arylthio, lower alkylsulfonyl; arylsulfonyl; lower alkylsulfonyamino, arylsulfonylamino, cycloalkylsulfonylamino, carboxy, unsubstituted and substituted carbamoyl and sulfamoyl, lower alkoxycarbonyl, hydrogen, lower alkanoyloxy, amino, alkylamino, arylamino, dialkylamino, substituted alkylamino, or substituted arylamino. For example, R and R' can be independently selected from the group consisting of hydrogen, substituted or unsubstituted alkyl, substituted or unsubstituted aryl, and substituted or unsubstituted alkyl-aryl. In certain embodiments, R and R' can be independently selected from the group consisting of methyl, ethyl, propyl, butyl, phenylethyl, phenyl-propyl, phenyl-butyl, and phenyl-sulfite.

In some embodiments, R and R' are independently selected from substituted or unsubstituted alkyl and alkylaryl; and R" and R'" are independently selected from hydrogen; halogen; alkyl, —OR$^1$; —NR$^1$R$_2$; —CN; —C(=O)OR$^1$; —OC(=O)R$^1$; C(=O)R$^1$; —SO$_2$R$^1$; —SO$_2$NR$^1$R$_2$; and —NR$^1$SO$_2$R$^2$; wherein R$^1$ and R$^2$ are individually hydrogen; or substituted or unsubstituted alkyl. In some embodiments, R" and R'" can all be hydrogen.

In some embodiments, R" and R'" are not the same. In some embodiments, R' and R' are not the same. For example, R can be ethyl and R' is propyl or butyl. In some embodiments, when R is a substituted or unsubstituted methyl, R' is not a substituted or unsubstituted methyl; when R is a substituted or unsubstituted ethyl, R' is not a substituted or unsubstituted ethyl; when R is a substituted or unsubstituted propyl, R' is not a substituted or unsubstituted propyl; when R is a substituted or unsubstituted butyl, R' is not a substituted or unsubstituted butyl; and so forth. In some embodiments, when R" is hydrogen, R'" is not hydrogen; when R" is a carboxylate, R'" is not a carboxylate; when R" is a sulfate or sulfonate, R'" is not a sulfate or sulfonate; when R" is a phosphate or phosphonate, R'" is not a phosphate or phosphonate; when R" is an alkoxy group, R'" is not an alkoxy group. In some embodiments, when R' and R' are the same, A is not hydrogen or a carboxylate group.

In some embodiments, n and m can independently be 0, 1, 2, 3, 4, 5, or 6.

In some embodiments, R, R', R", and R'" can be independently charged. In some examples, R, R', R", and R'" can independently include a cationic or an anionic group. In some embodiments, R, R', R", and R'" can include a cationic group such as a quaternary ammonium group or an iminium group. In some embodiments, R, R', R", and R'" can independently include an anionic group such as sulfonate, sulfate, borate, carboxylate, phosphonate, phosphate, thioacetate, thiols, thiosulphate, oxalate, nitro group, alkoxide, salts thereof, and combinations thereof. In some examples, the compound represented by Formula IV or IVa can include a plurality of cations. In some examples, the compound can include one, two, three, four, or more cationic groups.

In some examples, the compound can have a structure according to Formula V:

Formula V or a salt or a hydrate thereof, wherein R and R' are independently selected from the group consisting of hydrogen; substituted or unsubstituted alkyl; substituted or unsubstituted cycloalkyl; substituted or unsubstituted alkenyl; substituted or unsubstituted alkynyl; substituted or unsubstituted heterocyclyl; substituted or unsubstituted cycloalkenyl; substituted or unsubstituted heterocycloalkenyl; substituted or unsubstituted aryl; substituted or unsubstituted heteroaryl; substituted or unsubstituted heteroalkyl; substituted or unsubstituted alkylaryl; substituted or unsubstituted alkylheteroaryl; and wherein A, R" and R'" can be independently selected from the group consisting of hydrogen; alkyl, —OR$^1$; —NR$^1$R$_2$; —NR$^1$R$^2$R$_3$; —NO$_2$; —CF$_3$; —CN; —C$_2$R'; —SR'; —N$_3$; C(=O) R$^1$; —C(=O)O R$^1$; —OC(=O) R$^1$; —O(CR$^1$R$_2$)$_r$C(=O) R$^1$; —C(=O)NR$^1$R$_2$; —NR$^1$C(=O) R$^2$; —O(CR$^1$R$_2$)$_r$NR$^2$C(=O)R'; —O(CR$^1$R$_2$)$_r$NR$^2$SO$_2$R'; —OC(=O)NR$^1$R$_2$; —NR$^1$C(=O)OR$^2$; —SO$_2$R'; —SO$_2$NR$^1$R$_2$; and —NR$^1$SO$_2$R$^2$; wherein R$^1$, R$^2$, and R$^3$ are individually hydrogen; substituted or unsubstituted alkyl; alkenyl; alkynyl; cycloalkyl; heterocyclyl; cycloalkenyl, heterocycloalkenyl, aryl, heteroaryl, arylalkyl, heteroalkyls, aryl, alkylaryl, alkylheteroaryl; and r is an integer from 1 to 6.

R and R' can be the same or different. In some embodiments, R and R' can all be hydrogen.

In some embodiments, R and R' can be independently selected from hydrogen, lower alkyl, lower alkoxy, halogen, aryloxy, lower alkylthio, arylthio, lower alkylsulfonyl; arylsulfonyl; lower alkylsulfonyamino, arylsulfonylamino, cycloalkylsulfonylamino, carboxy, unsubstituted and substituted carbamoyl and sulfamoyl, lower alkoxycarbonyl, hydrogen, lower alkanoyloxy, amino, alkylamino, arylamino, dialkylamino, substituted alkylamino, or substituted arylamino. For example, R and R' can be independently selected from the group consisting of hydrogen, substituted or unsubstituted alkyl, substituted or unsubstituted aryl, and substituted or unsubstituted alkyl-aryl. In certain embodiments, R and R' can be independently selected from the group consisting of methyl, ethyl, propyl, butyl, phenylethyl, phenyl-propyl, phenyl-butyl, and phenyl-sulfite.

In some embodiments, R and R' are independently selected from substituted or unsubstituted alkyl and alkylaryl; and R" and R'" are independently selected from hydrogen; halogen; alkyl, —OR$^1$; —NR$^1$R$_2$; —CN; —C(=O)OR$^1$; —OC(=O)R$^1$; C(=O)R$^1$; —SO$_2$R$^1$; —SO$_2$NR$^1$R$_2$; and —NR$^1$SO$_2$R$^2$; wherein R$^1$ and R$^2$ are individually hydrogen; or substituted or unsubstituted alkyl. In some embodiments, R" and R'" can all be hydrogen.

In some embodiments, A is selected from hydrogen; halogen; alkyl, —OR$^1$; —NR$^1$R$_2$; —CN; —C(=O)OR$^1$; —OC(=O)R$^1$; C(=O)R$^1$; —SO$_2$R$^1$; —SO$_2$NR$^1$R$_2$; and —NR$^1$SO$_2$R$^2$; wherein R$^1$ and R$^2$ are individually hydrogen; or substituted or unsubstituted alkyl. In some examples, A can be a halogen, such as fluoride, chloride, or bromide. In some examples, A can be hydrogen.

In some embodiments, R" and R'" are not the same. In some embodiments, R' and R' are not the same. For example, R can be ethyl and R' is propyl or butyl. In some embodiments, when R is a substituted or unsubstituted methyl, R' is not a substituted or unsubstituted methyl; when R is a substituted or unsubstituted ethyl, R' is not a substituted or unsubstituted ethyl; when R is a substituted or unsubstituted propyl, R' is not a substituted or unsubstituted propyl; when R is a substituted or unsubstituted butyl, R' is not a substituted or unsubstituted butyl; and so forth. In some embodiments, when R" is hydrogen, R'" is not hydrogen; when R" is a carboxylate, R'" is not a carboxylate; when R" is a sulfate or sulfonate, R'" is not a sulfate or sulfonate; when R" is a phosphate or phosphonate, R'" is not a phosphate or phosphonate; when R" is an alkoxy group, R'" is not an alkoxy group. In some embodiments, when R' and R' are the same, A is not hydrogen or a carboxylate group.

In some embodiments, R, R', R", and R'" can be independently charged. In some examples, R, R', R", and R'" can independently include a cationic or an anionic group. In some embodiments, R, R', R", and R'" can include a cationic group such as a quaternary ammonium group or an iminium group. In some embodiments, R, R', R", and R'" can independently include an anionic group such as sulfonate, sulfate, borate, carboxylate, phosphonate, phosphate, thioacetate, thiols, thiosulphate, oxalate, nitro group, alkoxide, salts thereof, and combinations thereof. In some examples, the compound represented by Formula V can include a plurality of cations. In some examples, the compound can include one, two, three, four, or more cationic groups.

Compositions comprising one or more of the compounds disclosed herein are also provided. The compositions can also include a near infrared compound that can exhibit a redshifted absorption and/or emission relative to conventional near infrared compounds, such as those described in U.S. Pat. Nos. 5,336,714 and 5,990,197, which are hereby incorporated herein by reference. In some embodiments, the composition can be an ink.

In some embodiments, the composition can include one or more of the compounds described herein and an acceptable carrier. In some embodiments, the composition can include one or more of the compounds described herein, a polymer, and an acceptable carrier.

The polymer can be a natural or synthetic polymer. The polymer can be a homopolymer or a copolymer comprising two or more monomers. The copolymer can be random, block, or comprise a combination of random and block sequences. The polymer can in some embodiments be linear polymers, branched polymers, or hyperbranched/dendritic polymers. The polymer can also be present as a crosslinked polymer. In some examples, the polymer can be a water dispersible polymer.

In some embodiments, the polymer can be charged. In some examples, the polymer can have a negative charge. The polymer can have a charge density of about 0.1 meq/g or greater at a pH of 7.0. For example, the polymer can have a charge density of about 0.2 meq/g or greater, about 0.5 meq/g or greater, about 0.75 meq/g or greater, about 1 meq/g or greater, about 1.5 meq/g or greater, about 2 meq/g or greater, or about 2.5 meq/g or greater at a pH of 7.0. The polymer can have a weight average molecular weight of from about 1,000 Da or greater. For example, the polymer can have a weight average molecular weight of from about 2,000 Da or greater, about 5,000 Da or greater, about 7,500 Da or greater, about or 10,000 Da or greater. In some embodiments, the polymer can have a weight average molecular weight of about 10,000 Da to about 1,000,000 Da (e.g., about 10,000 Da to about 500,000 Da, about 10,000 Da to about 250,000 Da, about 50,000 Da to about 250,000 Da, or about 50,000 Da to about 200,000 Da). For instance, in relation to powder coatings, the polymer can be from about 5,000 to about 15,000 Da; in relation to solvent based coatings, the polymer can be from about 1,000 to about 50,000 Da, such as about 1,000 to about 35,000 Da; and in relation to emulsion based coatings, the polymer can be in a range of from about 50,000 to about 10,000,000 Da, such as about 500,000 to about 2,000,000 Da.

Examples of suitable polymers can include substituted and unsubstituted polyamides, polyimides, polyesters, polyacrylates, polyacrylic acids, polyethers, vinylic polymers, polyimines, polysiloxanes, polyurethanes, polythioethers, polycarbonates, polyolefins, polyarylalkylenes, polysilanes, polyesteramides, polyacetal, polysulfones, polystyrenes, polyacrylamides, polyvinyl alcohols, polyphosphonite, polyphosphonate, cellulose, derivatives thereof, copolymers thereof, and blends thereof. In some embodiments, the polymer can include polyethylene, polypropylene, polyethylene oxide, polyethylene glycol, polypropylene oxide, polythiourethane, polythioureas, polydithiourea, cellulose ether, cellulose ester, polyether ketone, derivatives thereof, copolymers thereof, and blends thereof.

In some examples, the polymer can include one or more anionic group such as sulfonate, sulfate, borate, carboxylate, phosphonate, phosphate, thioacetate, thiols, thiosulphate, oxalate, nitro group, alkoxide, salts thereof, and combinations thereof.

The compound can be covalently or non-covalently linked to the polymer. For example, the compound can be linked to the polymer by electrostatic forces, dipole-dipole interactions, hydrogen bonding, hydrophobic interactions, van der Waals forces, or combinations thereof. In some embodiments, the polymer includes a functional group reactive with the compound in the composition. In some examples, the compound includes an ionic group that interacts through electrostatic forces with the polymer.

The term "carrier" as used herein, includes aqueous or non-aqueous solutions, dispersions, suspensions, emulsions, and solids. In some embodiments, the carrier can include an aqueous solvent. In some embodiments, the carrier can include water, an alcohol, mixtures of water and organic co-solvents, high boiling organic solvents such as hydrocarbons, esters, ketones, or combinations thereof. In some examples, the solvent can include water, a $C_1$-$C_5$ alkyl alcohol, a $C_3$-$C_5$ ketone, a $C_3$-$C_6$ ester, or mixtures thereof.

In some embodiments, the composition can comprise one or more of the compounds described herein, a polymer, and a solvent. In some embodiments, the polymer can be soluble in the carrier and capable of forming a single phase material. In some embodiments, the compound can be dispersed or dissolved in the composition.

The compositions described herein can include other auxiliaries such as salts, metal oxides, fillers, rheology modifiers, surfactants, biocide, humectants, corrosion inhibitors, and other suitable adjuvants.

The compound can be present in the composition in an amount of from about 0.001% or greater by weight of the composition, for example, about 0.001% to about 5%, about 0.01% to about 5%, about 0.1% to about 5%, about 0.001% to about 4%, about 0.001% to about 3%, about 0.01% to about 2%, or about 0.01% to about 1%, by weight of the composition.

The polymer can be present in the composition in an amount of from about 0.01% or greater by weight of the composition, for example, about 0.1% or greater, about 0.5% or greater, about 1% or greater, about 5% or greater, about 10% or greater, or about 15% or greater. In some embodiments, the polymer can be present in the composition in an amount of from about 99% or less by weight of the composition, for example, about 95% or less, about 85% or less, about 75% or less, about 65% or less, about 50% or less, or about 30% or less. In some embodiments, the polymer can be present in the composition in an amount of from about 0.1% to about 99%, about 0.1% to about 95%, about 0.1% to about 90%, about 0.1% to about 80%, about 0.1% to about 50%, about 0.1% to about 20%, or about 1% to about 25%, by weight of the composition.

The carrier can be present in the composition in an amount of from about 1% or greater by weight of the composition, for example, about 2% or greater, about 5% or greater, about 10% or greater, about 15% or greater, about 20% or greater, or about 30% or greater. In some embodiments, the carrier can be present in the composition in an amount of from about 99% or less by weight of the composition, for example, about 95% or less, about 85% or less, about 75% or less, about 65% or less, about 50% or less, or about 30% or less. In some embodiments, the carrier can be present in the composition in an amount of from about 0.1% to about 99%, about 10% to about 99%, about 25% to about 99%, about 50% to about 99%, or about 75% to about 99%, by weight of the composition.

Methods of making the compositions are also disclosed herein. The method can include dissolving the polymer in a first solvent to form a polymer solution (also referred to herein as a first solution). The polymer solution may be heated to aid dissolution of the polymer. The first solution can be heated up to the boiling point of the first solvent. The first solvent can be the carrier in the ink composition. In some embodiments, the first solvent can include water, an alcohol, a ketone, an ester, or combinations thereof.

The method can also include dissolving the near infrared compound in a second solvent to form a near infrared solution (also referred to herein as a second solution). The near infrared solution can be heated to aid dissolution of the compound. In some embodiments, the second solvent can be the same as the same solvent. In some embodiments, the second solvent can be a volatile organic solvent. For example, the second solvent can be dichloromethane, ethyl acetate, an alcohol, a ketone, an ester, a hydrocarbon, or combinations thereof.

The method can also include adding the near infrared solution to the polymer solution. In some embodiments, the method can also include cooling the polymer solution before adding the second solution. A third solvent can be added to the polymer solution before, simultaneously, or after adding the near infrared solution.

The method can also include evaporating the second solvent. The second solvent can be evaporated by heating or exposure of the mixture to a vacuum or air.

The methods described herein can provide for the dispersion of the near infrared compound in a water-dispersible polymer without requiring the near infrared compound to be present during a polymerization process. These methods can be used to prepare compositions without subjecting the near infrared compound to a high temperature copolymerization and dispersion processes. These methods can provide for more economical production of ink and coating compositions containing near infrared absorbing and fluorescent dyes, including dyes that can lack the thermal stability to be present during standard polymerization conditions (e.g., a dye, such as a carbocyanine, that can be thermally decomposed during polymerization). The compositions can exhibit unexpectedly superior solubility and fluorescence properties.

Methods of using the compounds and compositions disclosed herein are also described. In some examples, the near-IR compounds can be molecularly dispersed in a water-dissipatable polymer such as a sulfo-containing polyester, polyester-amide, cellulose ester, polyester, or any other resin that may be soluble in a solvent such as an alcohol, ketone, or ester solvent. In some embodiments, the composition can be used as cosmetics, inks, for example security printing inks, plastics and paints. In some examples, the compositions can be used for marking a surface by printing, spraying, painting, or other methods for the purpose of detection, identification, or authentication of objects. Methods for detecting, identifying, or authenticating an article can include applying a compound or composition disclosed herein to a first portion of the article. The method can also include illuminating the first portion of the article with an excitation light source, to emit near infrared light at a first wavelength. The first wavelength is specific to the compound or composition used, and is configured to detect, identify, or authenticate the article.

EXPERIMENTAL

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1: Near Infrared Absorbing Dyes

The following near infrared absorbing and fluorescent compounds can be synthesized:

Formula IA

R = benzyl, 2-phenyl-ethyl, 3-phenyl-propyl, aryl-alkyl-
R' = —H, —R, —OR, —$CO_2R$, —$SO_2R$, —$SO_2NHR$, —$SO_2NR_2$, —COR, —$NR_2$, —CN

2 = MHI-93

Formulae IA provides a generalized structure of squaraine dye MH-93 where R=arylpropyl, heterocyclic ring substituents alkyl, alkyl-aryl, O-alkyl, O-alkyl-aryl, N-Halkyl, N-Halkyl-aryl, N(alkyl)$_2$, N(alkyl-aryl)$_2$, CO$_2$-alkyl, NHaryl, etc.

Formula IIA

R = Butyl, MHI = 06
R = Ethyl, MHI = 21
R = Phenylpropyl, MHI=36

Formula IIB

R = Butyl
R = Ethyl
R = Phenylpropyl

Formula IIC

R = Butyl
R = Ethyl
R = Phenylpropyl

Formulae IIA-IIC provide a generalized structure of carbocyanine dyes such as tri-carbocyanines MH 36, MH 88, MH 06, MH83, MH21, pentacyanine —N—CH2CH2CH2-phenyl iodide, and heptacyanines such as MH133; and Fischer Base type pentacyanine and heptacyanine types: R and heterocyclic ring substituents as for I above.

R = phenyl propyl, ethyl, butyl
R = Me, MHI-128

R = phenyl propyl, ethyl, butyl
R = Me, MHI-84

MHI-133

MHI-118

The near infrared absorbing and fluorescent compounds shown above can be synthesized as shown in Schemes 1-3.

Scheme 1. General synthesis of squaraine dye MH-93.

MHI-93

Compounds where R is arylpropyl, heterocyclic ring substituents alkyl, alkyl-aryl, O-alkyl, O-alkyl-aryl, N—H alkyl, N—H alkyl-aryl, N(alkyl)$_2$, N(alkyl-aryl)$_2$, CO$_2$-alkyl, N—H aryl, etc. can also be synthesized using a similar method.

Scheme 2. General synthesis of tricarbocyanine, pentacyanine, and heptacyanine dyes and Fischer Base type pentacyanine and heptacyanine dyes.

1
83%
R = phenylpropyl-, ethyl, butyl

Scheme 3. General synthesis of tricarbocyanine, pentacyanine, and heptacyanine dyes and Fischer Base type pentacyanie and heptacyanine dyes.

38
R = phenypropyl, ethyl, butyl

Compounds where R is arylpropyl, heterocyclic ring substituents alkyl, alkyl-aryl, O-alkyl, O-alkyl-aryl, N—H alkyl, N—H alkyl-aryl, N(alkyl)$_2$, N(alkyl-aryl)$_2$, CO$_2$-alkyl, N—H aryl, etc. can also be synthesized using a similar method.

The strategy described in Scheme 1 can be used to prepare near infrared absorbing and fluorescent dyes that exhibit a further increase the wavelengths of maximum absorption and emission of the inks and coating compositions. The fluorescence emission detected (signal) is greatly enhanced over background emission (noise). This increased fluorescence signal to noise ratio was achieved by design of the improved heterocyclic intermediates for inclusion into the dye compositions of types MH 93 and MH36 and also permits a lower energy of activation and emission (less background fluorescence and increased signal to noise during detection from printed inks or applied coatings), and unexpected solubility improvement when compared to NIRF dyes described in U.S. Pat. Nos. 5,336,714 and 5,990,197.

An additional advantage of these longer wavelength dyes is that in the longer wavelength range of the electromagnetic spectrum the background color has less influence. Most of dyes used in surface colorations do not have significant absorbance over 900 nm, making all surfaces uniformly gray looking as observed by the viewer. For example, shorter wavelength NIR dyes on dark surfaces cannot be detected at all or they give a very weak signal.

TABLE I

Properties of Dyes MH-93 MH-36

| Dye # | λmax, absorption (solvent) | λmax, emission (solvent) | Relative Intensity (MH93 = 100) | Solubility (ppm) |
|---|---|---|---|---|
| MHI-36 | 759 nm (MeOH) | 780 nm (MeOH) | | |
| MHI-93 | 858 nm (MeOH) | 880 nm (MeOH) | | |

These dyes can exhibit improved solubility and fluorescence properties relative to the NIRF dyes described in U.S. Pat. Nos. 5,336,714 and 5,990,197. The dyes can be used for formulation of water-based and organic solvent-based inks and coating compositions using a processes that allow for the molecular dispersion of the dyes in polymers, such as polyester and cellulose ester polymers.

The dye molecules can be dispersed in water-dissipatable polyesters. Due to the hydrophobic character of the NIR dyes, once the dye is inside of the polymer particle, it will remain dispersed in the polymer for a long period of time. Our data indicate that inks made with this procedure are stable for at least five years in aqueous solutions, and indefinitely once the ink is dry.

Process for Molecular Dispersion of Organic Dyes in Water-Dissipatable Polyesters and Polyester-Amides The General Process Procedures to Make NIRA, NIRB, NIRC AQ55 S Inks in Water:

1. In 2 L round bottom flask containing 800 mL nano pure water, 200 g of AQ55 S resin will be added at 80-90° C.
2. Continue heating until the resin completely dissolve
3. Cool down to room temperature.
4. In a flask dissolve 250 mg of the dye in dichloromethane (100 mL).
5. In another flask put ethyl acetate (100 mL)
6. The dye solution in dichloromethane, the ethyl acetate solution will be added at the same time dropwise to the resin solution with vigorous stirring
7. After the solutions addition completed the mixture will continue stirring for 2 days, then gravity filtration
8. Before the storage process, the ink must be free from dichloromethane and ethyl acetate Process for Molecular Dispersion of Organic Dyes in Organic Solvent Soluble Polyesters and Cellulose Esters The General Process Procedures Here to Make NIRA, NIRB, NIRC CAB Inks in Ethanol:

1. Dissolve the CAB (15 g, 1.5%) in (1 kg, 1266 mL) ethanol at 50° C.
2. Dissolve 400 mg of the dye in dichloromethane (100 mL)
3. The dye solution in dichloromethane will be added slowly to the CAB resin solution.
4. Continue heating the ink mixture at 50° C., for 2-3 h
5. The ink will cool down to room temperature, then gravity filtration
6. Before the storage process, the ink must be free from dichloromethane.

Provided Herein are the Following Exemplary Items:
1. A coating composition useful for marking surfaces of objects by printing, spraying, painting, or other processes for the purpose of identification and authentication of objects comprising
   (I) about 1 weight percent to about 25 weight percent of a water-dissipatable polyester comprising:
      (i.) monomer residues of at least one dicarboxylic acid;
      (ii.) about 4 to 25 mole percent, based on the total of all acid, hydroxy and amino equivalents, of monomer residues of at least one difunctional sulfo monomer containing at least one sulfonate group bonded to an aromatic ring where the functional groups are hydroxy, carboxyl or amino;
      (iii.) monomer residues of at least one diol or a mixture of a diol and a diamine; and optionally,
      (iv.) monomer residues of at least one difunctional monomer reactant selected from hydroxycarboxylic acids, aminocarboxylic acids and aminoalkanols;
   provided that at least 20 percent of the groups linking the monomeric units are ester linkages; said water dissipatable polyester having from about 0.1 ppm by weight to about 10% by weight of a near infrared fluorophoric compound molecularly dispersed therein by a phase partition dyeing process itemized below; and
   (II.) About 75 weight percent to about 99 weight percent of water.
2. The coating composition of item 1, wherein component iii. is comprised of
   (a) at least 15 mole percent, based on the total mole percent of diol monomer residues or diol and diamine monomer residues, of a diol having the formula —(OCH$_2$CH$_2$)n- where n is 2 to about 20, or
   (b) about 0.1 to less than about 15 mole percent, based on the total mole percent of diol monomer residues or diol and diamine monomer residues, of monomer residues of a poly(ethyleneglycol) having the formula —(OCH$_2$CH$_2$)n- where n is 2 to about 500, provided that the mole percent of such residues is inversely proportional to the value of n.
3. The coating composition of item 1 or 2, wherein near infrared fluorophoric compound is a compound defined above.
4. The coating compositions of item 1-3 prepared by a new solvent dyeing process for molecular dispersion of the dyes described in Formulae I, II, III, IIIa, IIIb, and IIIc that have adequate solubility in processing solvents methylene dichloride and ethyl acetate and equilibrium partition coefficients to permit complete phase transfer of the dye into the swollen polymer dispersed in water at 20 to 35 C followed by removal of volatile organic solvents.
5. Ink jet printing ink compositions of matter comprising:
   A. from about 0.5 to 10.0 weight percent of at least one water dissipatable polyester comprising:
      (i) monomer residues of at least one dicarboxylic acid;
      (ii) about 4 to 25 mole percent, based on the total of all acid, hydroxy and amino equivalents, of monomer residues of at least one difunctional sulfomonomer containing at least one sulfonate group bonded to an aromatic ring where the functional groups are hydroxy, carboxyl, carboxylate ester or amino;
      (iii) monomer residues of at least one diol or a mixture of diol and a diamine; and optionally,
      (iv) monomer residues of at least one difunctional monomer reactant selected from the group consisting of hydroxycarboxylic acids, amino carboxylic acids and aminoalkanols;
      provided that at least 20 percent of the groups linking the monomeric units are ester linkages;
      and said water-dissipatable polyester having from about 0.1 ppm by weight to about 2% by weight of a near infrared fluorophore molecularly dispersed therein by the process of item 4.
   B. between about 5 and 75 weight percent of at least one aliphatic humectant;
   C. between about 0 and 15 weight percent of at least one lower aliphatic alcohol of no more than 3 carbon atoms;
   D. water and optionally up to about 2 weight percent of one or more additives; wherein the weight percentages of components A-D equal 100%.
6. The ink composition of item 5 wherein said water-dissipatable polyester is a sulfopolyester and wherein the diol of component (iii), based upon 100% diol comprises
   (a) at least 15 mole percent of a diol having the formula H(OCH$_2$CH$_2$)$_n$OH, where n is 2 to about 20, or
   (b) about 0.1 to less than about 15 mole percent of a poly(ethylene glycol) having the formula H(OCH$_2$CH$_2$)$_n$OH, where n is 2 to about 500, provided that the mole percent of said poly(ethylene glycol) is inversely proportional to the value of n.
7. The ink composition of item 5 comprising:
   A. said water dissipatable polyester;
   B. between about 45 and 75 weight percent of said humectant;
   C. between about 2 and about 15 weight percent of said lower aliphatic alcohol;
   D. water; between about 0.01 and about 0.50 weight percent of at least one corrosion inhibitor; and between about 0.01 and about 0.30 weight percent of at least one biocide.
8. The ink composition of item 5 further comprising:
   A. said water dissipatable polyester;
   B. between about 4 and about 8 weight percent of said humectant;
   C. between about 0.35 and about 0.65 weight percent of at least one surface active agent;
   D. water; between about 0.75 and about 1.25 weight percent of at least one defoaming agent; between about 0.01 and about 0.5 percent of at least one corrosion inhibitor; and between about 0.01 and about 0.3 weight percent of at least one biocide.
9. The ink composition of item 5 wherein said humectant is selected from the group consisting of ethylene glycol, propylene glycol, butanediol, glycerol, polyethylene glycols of the formula H—(OCH2CH2)nOH having a number average molecular weight between 200 and 10,000; poly(ethylene glycol) methyl ethers having a number average molecular weight of about 250 to about 5,000; polyvinyl alcohols, polyvinylpyridines, and polyvinylpyrrolidones and mixtures thereof.
10. The ink composition of item 5 wherein said humectant is selected from the group consisting of ethylene glycol, propylene glycol, butanediol, glycerol, polyethylene glycols of the formula H—(OCH2CH2)n-OH wherein n is 2 to 6 and mixtures thereof.
11. The composition of item 5, wherein the near infrared fluorescing compound is selected from the group consisting of phthalocyanines, 2,3-naphthalocyanines, squaraines, and carbocyanines and correspond to Formulae I, II, III, IIIa, IIIb, and IIIc provided that the dye substituents have been selected so that adequate solubility in the processing solvents methylene dichloride and ethyl acetate is achieved to permit successful operation of the process of item 4.

12. The composition of item 5, wherein the near infrared fluorescing compound is selected from the group consisting of squaraines and carbocyanines and correspond to Formulae I and II.
13. Ink Jet printing ink compositions of matter comprising:
   a) from about 0.5 to 10 percent of a non-sulfo containing, organic solvent soluble polyester having from about 0.1 ppm by weight to about 2% by weight of a near infrared fluorophore molecularly dispersed therein; or alternatively
   b) between about 0.5 and about 10 weight percent of a binder selected from a cellulose ester, a condensed phenolic resin, a polyketone, a polyamide, or a polyurethane polymer having from about 0.1 ppm by weight to about 2 weight percent of a near infrared fluorophore molecularly dispersed therein, and
   c) between about 0.01 and about 0.5 weight percent of a corrosion inhibitor;
   d) between about 0.50 and about 1.0 percent of an organic solvent soluble electrolyte; and
   e) the remainder of said composition having at least one $C_3$-$C_6$ aliphatic ketone, or at least one $C_3$-$C_6$ aliphatic ester, or at least one $C_1$-$C_3$ alcohol, or a combination thereof, wherein all weight percentages are based on the total weights of the constituents a-e. tripropylene glycol, polyethylene glycols having number average molecular weights from 100 to about 10,000 and polypropylene glycols having number average molecular weights
14. The composition of item 13 wherein said organic solvent soluble polyester comprises:
   a) monomer residues of at least one dicarboxylic acid selected from the group consisting of $C_6$-$C_{12}$ aliphatic dicarboxylic acids, 1,4-cyclohexane-dicarboxylic acid, $C_3$-$C_{12}$ oxa-aliphatic dicarboxylic acids which contain one or more oxygen atoms in the aliphatic chain and mixtures thereof; and
   b) monomer residues of at least one diol selected from the group consisting of diethylene glycol, triethylene glycol, dipropylene glycol, tripropylene glycol, polyethylene glycols having number average molecular weights from 100 to about 10,000 and polypropylene glycols having number average molecular weights of about 200 to about 6000.
15. The composition of item 13 wherein the amount of said near infrared fluorophore molecularly dispersed in the polymer phase is from about 100 ppm by weight to about 50,000 ppm by weight.
16. The composition of item 15 wherein said near infrared fluorophore molecularly dispersed in the polymer phase includes a functional group which is reactive with polyester end groups.
17. The composition of item 15 wherein said near infrared fluorophores are selected from the group consisting of phthalocyanines, 2,3-naphthalocyanines, squaraines, and carbocyanines corresponding to Formulae I, II, III, IIIa, IIIb, IIIc.
18. The composition of item 15 wherein said near infrared fluorophores are selected from the group consisting of carbocyanines corresponding to Formula II.
19. The composition of item 15 wherein said near infrared fluorophores are selected from the group consisting of squaraines corresponding to Formula I.
20. The compositions of item 17 formulated for use in an ink jet printer, said ink using optimized quantities of the ingredients described in item 13.
21. The compositions of item 18 formulated for use in an ink jet printer, said ink using optimized quantities of the ingredients described in item 13.
22. The compositions of item 19 formulated for use in an ink jet printer, said ink using optimized quantities of the ingredients described in item 13.
23. The compositions described in items 5-11 formulated for use in an ink jet printer, said ink using optimized quantities of the ingredients described in items 5-11.
24. The compositions described in items 5-10 and 12 formulated for use in an ink jet printer, said ink designed to use optimized quantities of the ingredients described in items 5-10 and 12.
25. A method for detecting, identifying, authenticating an article having a near infrared fluorescent ink printed thereon, said ink having detectable fluorescence when exposed to near infrared radiation, said method comprising the steps of:
   a) Applying to a surface of said article a fluorescing ink comprising:
   The ink of item 20, or item 21, or item 22, or item 23, or item 24, or alternatively, a mixture of the inks of items 20-24,
   b) Using an appropriate near infrared excitation light source to cause the ink to produce a detectable near infrared fluorescence, and
   c) using a detection means to detect said detectable near infrared fluorescence.
26. The method of item 25 wherein said article has porous surface characteristics.
27. The method of item 26 wherein said article has non-porous surface characteristics.

Throughout this application, various publications are referenced. The disclosures of these publications in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:
1. A compound of Formula I:

Formula I or a salt or a hydrate thereof,
wherein R and R' are independently selected from the group consisting of substituted or unsubstituted alkylaryl; substituted or unsubstituted alkylheteroaryl;
wherein R" and R'" are independently selected from the group consisting of hydrogen; halogen; alkyl, —$OR^1$;

—NR$^1$R$^2$; —NO$_2$; —CF$_3$; —CN; —C$_2$R$^1$; —SR$^1$; —N$_3$; C(=O)R$^1$; —C(=O)OR$^1$; —OC(=O)R$^1$; —O(CR$^1$R$^2$)$_r$C(=O)R$^1$; —C(=O)NR$^1$R$^2$; —NR$^1$C(=O)R$^2$; —O(CR$^1$R$^2$)$_r$NR$^2$C(=O)R$^1$; —O(CR$^1$R$^2$)$_r$NR$^2$SO$_2$R$^1$; —OC(=O)NR$^1$R$^2$; —NR$^1$C(=O)OR$^2$; —SO$_2$R$^1$; —SO$_2$NR$^1$R$^2$; and —NR$^1$SO$_2$R$^2$; wherein R$^1$ and R$^2$ are individually hydrogen; substituted or unsubstituted alkyl; substituted or unsubstituted alkenyl; substituted or unsubstituted alkynyl; substituted or unsubstituted cycloalkyl; substituted or unsubstituted heterocyclyl; substituted or unsubstituted cycloalkenyl, substituted or unsubstituted heterocycloalkenyl, substituted or unsubstituted aryl, substituted or unsubstituted heteroaryl, substituted or unsubstituted arylalkyl, substituted or unsubstituted heteroalkyl, or substituted or unsubstituted alkylheteroaryl; and r is an integer from 1 to 6, and wherein the compound of Formula I has a wavelength of maximum absorbance, $\lambda_{max}$, in the near infrared (NIR) region.

2. The compound of claim 1, wherein R and R' are independently selected from the group consisting of benzyl, phenyl-ethyl, phenyl-propyl, and phenyl-butyl.

3. The compound of claim 1, wherein the compound comprises an overall cationic charge.

4. A coating composition comprising a compound of claim 1, a polymer, and an acceptable carrier.

5. The composition of claim 4, wherein the compound interacts with the polymer through electrostatic forces, dipole-dipole interactions, hydrogen bonding, hydrophobic interactions, van der Waals forces, or combinations thereof.

6. The composition of claim 4, wherein the polymer includes a substituted or unsubstituted polyamide, polyimide, polyester, polyacrylate, polyacrylic acid, polyether, vinylic polymer, polyimine, polysiloxane, polyurethane, polythioether, polycarbonate, polyolefin, polyarylalkylene, polysilane, polyesteramide, polyacetal, polysulfone, polystyrene, polyacrylamide, polyvinyl alcohol, polyphosphonite, polyphosphonate, cellulose, derivatives thereof, copolymers thereof, or blends thereof.

7. The composition of claim 6, wherein the polymer comprises an anionic group.

8. The composition of claim 4, wherein the compound is in an amount of from about 0.001% to about 5% by weight of the composition.

9. A method of making the composition according to claim 4, comprising:
 a. dissolving the polymer in a first solvent to form a polymer solution,
 b. dissolving the compound in a second solvent to form a near infrared solution,
 c. combining the near infrared solution and the polymer solution,
 d. optionally evaporating the first solvent, the second solvent, or a combination thereof.

10. An article comprising a mark disposed on a first portion of the article, wherein the mark comprises a compound of claim 1.

11. The compound of claim 1, wherein R and R' are independently substituted and independently comprises a cationic quaternary ammonium group or an iminium group.

* * * * *